(12) United States Patent
Diaz et al.

(10) Patent No.: US 6,703,419 B1
(45) Date of Patent: Mar. 9, 2004

(54) CHEMICAL COMPOSITION FOR AIDING THE ABSORPTION, BINDING AND ELIMINATION OF UNDIGESTED FAT

(76) Inventors: Jose A. Diaz, 2950 Jackson Ave., Miami, FL (US) 33133; Eduardo M. Naranjo, 5009 SW. 71$^{st}$ Pl., Coconut Grove, FL (US) 33155

( * ) Notice: Subject to any disclaimer, the term of this patent is extended or adjusted under 35 U.S.C. 154(b) by 0 days.

(21) Appl. No.: 10/237,546

(22) Filed: Sep. 9, 2002

Related U.S. Application Data

(63) Continuation-in-part of application No. 09/808,646, filed on Mar. 13, 2001, now Pat. No. 6,447,812, which is a continuation-in-part of application No. 09/521,224, filed on Mar. 8, 2000, now Pat. No. 6,200,574, which is a continuation-in-part of application No. 09/135,920, filed on Aug. 18, 1998, now Pat. No. 6,048,532, which is a continuation-in-part of application No. 08/888,848, filed on Jul. 7, 1997, now Pat. No. 5,795,576.

(60) Provisional application No. 60/021,299, filed on Jul. 8, 1996.

(51) Int. Cl.$^7$ .................. A61K 31/34; A61K 35/12; A61K 35/64; A61K 35/78

(52) U.S. Cl. .................. 514/474; 424/520; 424/538; 424/725; 424/738; 424/777

(58) Field of Search .......... 514/474; 424/520, 424/538, 725, 738, 777

(56) References Cited

U.S. PATENT DOCUMENTS

| | | | |
|---|---|---|---|
| 5,795,576 A | * | 8/1998 | Diaz et al. ............ 424/195.1 |
| 6,048,532 A | * | 4/2000 | Diaz et al. ............ 424/195.1 |
| 6,200,574 B1 | * | 3/2001 | Diaz et al. ............ 424/195.1 |
| 6,447,812 B1 | * | 9/2002 | Diaz et al. ............ 424/725 |

* cited by examiner

*Primary Examiner*—Raymond Henley, III
(74) *Attorney, Agent, or Firm*—Malloy & Malloy, P.A.

(57) ABSTRACT

A composition and method for facilitating weight loss and aiding in the maintenance of a stable weight in humans, wherein a preferred embodiment of the chemical composition comprises a mixture of psyllium husks generally in an amount of between 72% and 88% by weight of the total chemical composition, natural marine shellfish extract generally in an amount of between 9% and 11% by weight, acacia generally in an amount of between 4.5% and 5.5% by weight, an amount of apple pectin generally in an amount of between 1.4% and 2.2% by weight of the total chemical composition, ascorbic acid (Vitamin C) generally in an amount of between 1.8% and 2.2% by weight. Magnesium stearate may also be included generally in an amount of about 1% by weight of the total chemical composition.

28 Claims, No Drawings

U.S. 6,703,419 B1

CHEMICAL COMPOSITION FOR AIDING THE ABSORPTION, BINDING AND ELIMINATION OF UNDIGESTED FAT

CLAIM OF PRIORITY

The present application is a continuation-in-part of U.S. patent application Ser. No. 09/808,646 and filed on Mar. 13, 2001, now U.S. Pat. No. 6,447,812, issued on Sep. 10, 2002, which is a continuation-in-part of U.S. Ser. No. 09/521,224 filed on Mar. 8, 2000 now U.S. Pat. No. 6,200,574, which is a continuation-in-part of U.S. patent application Ser. No. 09/135,920 filed on Aug. 18, 1998, now U.S. Pat. No. 6,048,532, which is a continuation-in-part of U.S. patent application Ser. No. 08/888,848 filed on Jul. 7, 19974, now U.S. Pat. No. 5,795,576 issued on Aug. 18, 1998, which claims priority under 35 U.S.C. Section 119(e) to provisional U.S. patent application Ser. No. 60/021,299 filed on Jul. 8, 1996. Each of these earlier patent applications are incorporated fully herein by reference.

BACKGROUND OF THE INVENTION

1. Field of the Invention

The present invention relates to a chemical composition and a method for aiding in absorbing and binding undigested fat for rapid elimination from the human body, and thereby assisting weight loss in humans. In accordance with the present invention, a human ingests the chemical composition in recommended dosages, preferably prior to eating a meal, so as to facilitate the binding of undigested fat to a fibrous agent for rapid elimination from the human body.

2. Description of the Related Art

In this day and age, many people's lifestyles have become less physically active due at least in part to the increasing demands of modern society. A natural result of a sedentary lifestyle is the tendency to gain weight. Indeed, it is now commonly thought that many people are over-weight and further, that obesity is becoming a growing problem. Due to this trend, countless efforts have been made to help people control their weight. As a few examples, many have proclaimed to have won the "battle of the bulge" with a specific diet program or a particular exercise program. Others have explored hypnosis and other mechanisms for controlling the appetite of an individual. Still others in the scientific arena have formulated sugar substitutes and are pursuing fat substitutes as methods to reduce the caloric intake of an individual hopefully, without sacrificing the taste of otherwise highly fattening foods. While these efforts are generally capable of aiding many in their fight to lose weight or to maintain a desired weight, many are in general, ineffective or simply not practical. For example, some good meaning souls have tried in earnest to follow a particular diet plan but eventually, fall off the plan lacking will-power to continue for weeks and months at a time. This is equally true of those who try hypnosis and similar weight-loss gimmicks. Finally, some view sugar substitutes as being tasteless or worse, as carrying an intolerable health risk, given that some studies have linked them to carcinogens and/or the formation of brain tumors.

It has been appreciated in recent years that the fat content of foods eaten are a major culprit behind human weight gain. For example, regardless of the type of fat present in a food product, fat has the highest caloric value per gram—about 9 calories per gram—of any food group. It is understood that the body tends to store fat for future use, rather than to utilize it immediately, and this factor helps lead to weight-gain. Additionally, in recent years it has further been recognized that there is a connection between the amount of fat stored in the body and the level of cholesterol in the body. A diet high in fat is more likely to result in the development of higher cholesterol levels. As cholesterol has been indicated as a factor in arteriosclerosis or hardening of the arteries, the risk for heart disease and/or a heart attack is elevated when a diet high in fat is followed. Unfortunately, fat also makes many food items more tasty—whether butter on bread, dressings on salads, sour cream on potatoes, or frosting on cake—and are, therefore, difficult to eliminate entirely from one's diet. Thus, fat usually finds its way into the body. Once it does so, a healthy body automatically secretes lipase, an enzyme that accelerates synthesis of fats, i.e., breaking down the fat molecule. The majority of all fats in foods are present in "triglyceride form", which the body seeks to break down by removing the glycerol molecule from the triglyceride and thereby, release the free fatty acids. Once this occurs, the body is well on its way to absorbing the fat and likely, storing same instead of utilizing it for energy.

From the foregoing, it will be understood that there remains an appreciable need in the art for a product which facilitates a person's efforts to lose weight and/or to control his or her weight and yet which is safe and easy to implement. There remains a need in the art for a product and method which aids a person in losing weight or in maintaining a stable weight, which does not rely exclusively on will power. Any such product or method should not interfere with the taste of foods. Ideally, any such product or method would permit a person to eat the foods that they most like, without being overly mindful of the fat content contained therein. Preferably, any such product or method would prevent the body from absorbing the fat in such foods once they have been eaten and further, would aid the body in rapid elimination of the absorbed fats in a safe and comfortable manner. In turn, the rapid elimination of fats subsequent to ingestion and prior to digestion, would have a highly beneficial effect in preventing the build-up or accumulation of harmful cholesterol. The present invention is designed to satisfy the needs in the art and is believed to represent a significant advance in improving a person's health by facilitating weight loss through the rapid elimination of the fat from the human body.

SUMMARY OF THE INVENTION

The present invention provides a novel, chemical composition for ingestion by humans which facilitates weight loss and fosters the maintenance of a stable weight in humans, although the invention should not be construed so as to be limited to use with humans. In particular, when the chemical composition of the present invention is ingested by a human prior to eating a meal, the composition acts to absorb and bind undigested fat to a fibrous agent so as to promote its rapid elimination from the human body.

In accordance with this invention, the novel composition is moisture activated such that it remains inert and can be formed into capsules, preferably conveniently sized for ingestion by a human, and will remain inert until it comes into contact with water, bodily fluids or other liquids. In one embodiment, the composition of the present invention comprises a mixture of a fibrous agent, preferably psyllium husks, in generally an amount of between 72% and 88% by weight of the total chemical composition, natural marine shellfish extract generally in an amount of between 9% and 11% by weight of the total chemical composition, acacia generally in an amount of between 4.5% and 5.5% by weight of the total chemical composition, apple pectin generally in an amount of between 1.4% and 2.2% by weight of the total chemical composition, ascorbic acid, better known as Vitamin C, generally in an amount of between 1.8% and 2.2% by weight of the total chemical composition, and magnesium stearate generally in an amount of about 1% by weight of the total chemical composition. Upon contact with moisture, the composition begins to break down and becomes activated. Once activated, the composition acts quickly, usually within 30 seconds to seek and attach itself to undigested fats such as oils and the like, and typically, within about 2 minutes will form a small mass of undigestible fibrous material. Additionally, a method for using the chemical composition is also described, which comprises the steps of forming a capsule or tablet containing between about 500 and 700 milligrams of the chemical composition and having a human ingest at least one to four of these capsules with generally about eight ounces of water generally about fifteen to about twenty minutes before a meal.

A primary object of the present invention is to provide a chemical composition and method of treatment which serve as a convenient and effective means for reducing the quantity of fat digested and/or absorbed by the human body.

Another primary object of the present invention is to provide a chemical composition which seeks out, attaches and binds undigested fat ingested by a human to a fibrous agent, forming an undigestible mass which can easily and rapidly be eliminated from the human's body.

A feature of the chemical composition according to the present invention is that it is moisture activated and therefore, is inert and can be formed into and stored as conveniently sized capsules, each containing generally between about 500 and 700 milligrams of the chemical composition, until being ingested by a human and activated by coming into contact with bodily secretions whether water or other liquid.

Yet another object of the present invention is to provide a chemical composition which includes at least one fibrous material for aiding the human body in rapid elimination of waste.

A feature of the present invention, is the ability of capsule containing approximately 500 milligrams of the chemical composition, to absorb up to twelve times its own weight or generally about 3 to 6 grams of undigested fats.

These and other objects, features and advantages of the present invention will become readily apparent from the detailed description, which follows.

DETAILED DESCRIPTION OF THE PREFERRED EMBODIMENTS

The present invention is directed towards a chemical composition for ingestion by humans which acts to absorb and bind undigested fat and rapidly eliminate the undigested fat from the human body. The present invention is also directed to a method of aiding weight loss in humans.

The chemical composition of the present invention primarily comprises at least one fibrous agent to act both as a vehicle for absorbing fat and as a medium for allowing a human to feel full. The fibrous agent may include any of a number of compounds including, but not limited to, psyllium, bran, ideally but not necessarily oat bran, the husks of natural oat bran seeds, as well as plantago ovata seed mucilage. Additional embodiments of the composition of the present invention are envisioned which may comprise one or more other fibrous agents.

At least one embodiment of the chemical composition comprises psyllium husks, a purified fiber product obtained from the dilute acid extract from the seeds of plantago ovata, as the fibrous agent. In a preferred embodiment, the psyllium husks comprise generally an amount of between 72% and 88% by weight and, ideally, an amount of about 80% of the total chemical composition. As previously indicated, however, it remains within the scope of the present invention for the chemical composition to comprise one or more other fibrous agents.

In addition to a fibrous agent, a preferred embodiment of the chemical composition of the present invention comprises natural marine shellfish extract ("NMSE"). In one preferred embodiment, NMSE is included generally present in an amount of between 9% and 11% by weight, and ideally, in an amount of about 10% by weight of the total chemical composition. The NMSE is obtained from shellfish such as, for example, crabs, shrimp, and/or lobsters, which are initially exposed to a deproteinization process comprising a dilute, approximately 3.5%, sodium hydroxide solution, which is maintained at a temperature between 80 and 90 degrees Celsius, into which the shellfish are placed for approximately 3 hours. Next, the shellfish are decalcified in a dilute, approximately 5% to 7%, hydrochloric acid solution, maintained at room temperature for approximately 2 hours. The shellfish are then deacylated in a concentrated, approximately 46% to 48%, sodium hydroxide solution, at a temperature between 85 and 95 degrees Celsius for a period of anywhere from 8 to 20 hours. Once the shellfish have been deacylated, the remaining extract is washed, dried, and is reduced to a powder form, ready for consumption.

An alternate embodiment of the present invention may comprise glucosamine, a material derived from deacetylated shellfish shells or chitin. Chitin is known in the art as a naturally occurring polysaccharide—a polymer of long molecules consisting of sugar molecules strung together as shown by the general formula:

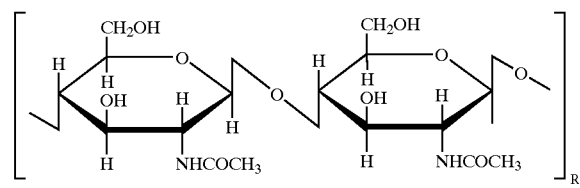

Chitin, which can be obtained from crab, lobster or shrimp shells by dissolving the shells with calcium carbonate and then removing protein fragments, leaving behind chitin as a white powder, normally cycles through the environment, decomposing naturally into its hydrogen, carbon, nitrogen and oxygen building blocks. In one process, glucosamine may be obtained from chitin by hydrolysis. Specifically, glucosamine salts and compounds are derived from a monomer of chitin, namely, N-acetyl-D-glucosamine (GlcN Ac) which is represented by the general formula:

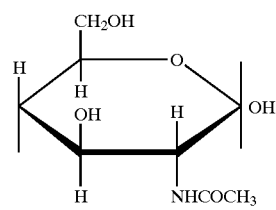

and will be utilized such as, for example, glucosamine hydrochloride, acetylated glucosamine, and/or D-glucosamine. Glucosamine hydrochloride has been shown to be an efficacious alternative to corticosteroid treatment of enteritis and colonitis. It will be understood by those of ordinary skill in the art that as a derivative of chitosan, which has an ability to chelate various metal ions because its hydroxy and amino groups act as electron donors, glucosamine HCl is an ion, or a molecule having a negative charge which, therefore, attracts and binds with certain molecules of food. In another alternate embodiment, a beta-alkylglycoside of N-acetyl-D-glucosamine may be utilized, which is represented by the general formula:

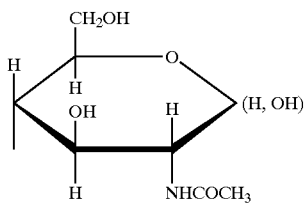

and is believed to effectively increase the ability of one's digestive tract to handle substantial quantities of lactose. In yet another alternate embodiment, the composition may comprise chitosan which is formed by subjecting chitin, in white powder form, to a concentrated sodium hydroxide solution heated to above 135 degrees Celsius to remove one of chitin's side groups, i.e., to hydrolize the N-acetyl, which can be more readily dissolved. Chitosan, which is represented by the general formula:

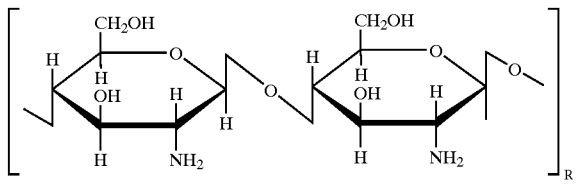

also has the ability to act as a coagulant, i.e., to attract and bind with certain molecules, such as amino acids and proteins.

In addition to psyllium husks and NMSE, at least one embodiment of the present invention comprises acacia, more commonly known as karaya gum, generally in an amount of between 4.5% and 5.5% by weight of the total chemical composition. The acacia serves the purpose of providing lubrication and as well as providing an additional fibrous agent to the composition. In a preferred embodiment, acacia comprises an amount of about 5% by weight of the total chemical composition. An alternate embodiment of the present invention comprises glucomannan, also known as Konjak or Konjac Root, in lieu of acacia.

In addition, a preferred embodiment of the chemical composition also comprises a pectin obtained from fruits or vegetables which serves the purpose of providing an additional fibrous agent to the composition. The fruit or vegetable pectin is included in the chemical composition and comprises generally an amount of between 1.4% and 2.2% by weight. In a preferred embodiment, an apple pectin is included in amount of about 2% by weight of the total chemical composition.

The preferred embodiment of the composition also comprises ascorbic acid, better known as Vitamin C, generally in an amount of between 1.8% and 2.2% by weight, and ideally, in an amount of about 2% by weight of the total chemical composition. Ascorbic acid (Vitamin C) is provided in the preferred chemical composition to enhance the binding ability of the NMSE, glucosamine HCl, and/or chitosan.

Finally, at least one embodiment of the present invention comprises magnesium'stearate, which serves to make the resultant composition smooth. In one preferred embodiment, magnesium stearate comprises an amount of about 1% by weight of the total chemical composition. An alternate embodiment of the invention may comprise a saturated fatty acid, such as stearic acid, for the purpose of making the composition smooth.

In the most preferred embodiment, the psyllium husks, NMSE, acacia, apple pectin, ascorbic acid (Vitamin C), and magnesium stearate are mixed together in powder form, although a granular form might also be suitable, which results in a mixture which is inert until it comes into contact with water, or another liquid, such as is produced by the human body during digestion. Thus, in the most preferred embodiment, the present invention can be formed into capsules so as to facilitate packaging, storage and ingestion. Additionally, the material used to form the encasement of the capsule will be inert and upon coming into contact with water or other liquid, will begin to break down and permit both the release and activation of the chemical composition. If desired, the capsules containing the chemical composition according to the present invention may be packaged into bottles containing 50, 60, 75, 80, 100 or more capsules, and may include a small, separately wrapped quantity of a drying agent, such as a silica gel in order to aid dry conditions for preserving the composition inert until use by a human.

In one preferred embodiment of the present invention, a white opaque capsule, size No. 0, having a weight of approximately 100 milligrams (mg), is filled with a mixture comprising approximately 400 mg of psyllium husks; 50 mg of NMSE; 25 mg of acacia; 10 mg each of apple pectin and ascorbic acid (Vitamin C); and 5 mg of magnesium stearate, thereby yielding a capsule having a total weight of approximately 600 mg, and containing approximately 500 mg total of the chemical composition of the present invention. It will be appreciated that a capsule containing about 500 mg of the chemical composition has a size and overall dimension which is readily suited for being comfortably swallowed by a person, although the capsule could be formed to contain more or less of the chemical composition (with the ratios of the ingredients of the chemical composition similar to that disclosed herein) and thereby be somewhat larger or smaller, and still function in the intended manner when ingested by a person. Testing performed with the above described chemical compositions have demonstrated the ability to absorb up to 12 times its own weight or about 3 to 6 grams of undigested fats. For instance, in one experiment 70 milliliters of water was placed in an appropriately sized test tube along with 2 grams of wheat germ oil and 100 mg of lecithin. This mixture was shaken vigorously for about 10 seconds. Next, 1,000 mg of the chemical composition according to one embodiment of the present invention (two capsules containing 500 mg each) were added and again, the mixture was shaken vigorously for about 10 seconds. After several minutes, the mixture was observed as having approximately ninety-five (95%) percent of fat (oil layer) gone, i.e., fat was no longer visible but instead had become bound with the fibrous agent of the composition so as to form an undigestible mass.

In addition, the chemical compositions of the present invention lend themselves to a method of aiding human weight loss, which will now be described. In particular, the chemical compositions of the present invention seek out and bind with fat ingested by a human prior to its being absorbed into the body, and as has been explained, binds them to a fibrous agent so as to aid the person in feeling "full" and further, to permit rapid elimination by the human body.

A preferred method of the present invention comprises the steps of forming a capsule containing about 500 mg of the preferred chemical composition and having the human ingest at least one of the 500 mg capsules with generally about eight ounces of water generally about fifteen to twenty minutes before a meal. Ideally, the human will ingest one or two of the capsules before a meal, but may ingest up to about four of the capsules, or 2,000 mg of the chemical composition, if the meal to be eaten is especially large and/or has a particularly high fat content. Upon being ingested by a human, each capsule begins to disintegrate and releases or otherwise facilitates activation of the chemical composition contained therein, typically in about thirty (30) minutes, and often in less time. In one preferred embodiment of the present method, there is an additional step of having the human ingest generally about eight ounces of water upon waking up in the morning, and ideally, there is an additional step of having the human ingest generally about eight ounces of water between meals.

Another embodiment of the method of the present invention utilizes capsules containing about 700 mg of the chemical composition comprising psyllium husks generally in an amount of between 72% and 88% by weight of the total chemical composition, natural marine shellfish extract generally in an amount of between 9% and 11% by weight of the total chemical composition, acacia generally in an amount of between 4.5% and 5.5% by weight of the total chemical composition, apple pectin generally in an amount of between 1.4% and 2.2% by weight of the total chemical composition, ascorbic acid (Vitamin C) generally in amounts of between 1.8% and 2.2% by weight of the total chemical composition, and magnesium stearate generally in an amount of about 1% by weight of the total chemical composition. In this embodiment of the present invention, the capsule could be formed to contain more or less of the chemical composition (with ratios of the ingredients of the composition being similar to that disclosed herein), and thereby be somewhat larger or smaller and still be adequate for ingestion by a person.

In addition, this latter embodiment of the chemical composition of the present invention also lends itself to a method of aiding human weight loss by seeking out and binding with a fat ingested by a human prior to the fat being absorbed by the body. As has been explained, the fat binds to the fibrous agents of the composition so as to aid the person in feeling full, and further permits the rapid and natural elimination thereof from the human body. One method utilizing this latter embodiment of the present invention comprises the steps of forming a capsule containing about 700 mg of the chemical composition and having the human ingest at least 4 of the 700 mg capsules with generally about 8 ounces of water, approximately 15 to 20 minutes before a meal is to be consumed. From the foregoing, it should be clear that a human may ingest more than 4 of such capsules and even up to 6 or more of such capsules, if the meal to be eaten is especially large and/or has a particularly high fat content. Upon being ingested, each capsule begins to disintegrate and releases the chemical composition contained therein, in generally about 30 minutes and often less time. In one form of the method of the present invention utilizing this latter embodiment, there is an additional step of having the human ingest generally about 8 ounces of water upon waking in the morning and ideally, there is an additional step of having the human ingest about 8 ounces of water between meals.

Since many modifications, variations and changes in detail can be made to the described preferred embodiment of the invention, it is intended that all matters in the foregoing description be interpreted as illustrative and not in a limiting sense. Thus, the scope of the invention should be determined by the appended claims and their legal equivalents.

Now that the invention has been described.

What is claimed is:

1. A chemical composition for ingestion by a human at meal-times, which aids in absorbing and binding undigested fat for rapid elimination from the human's body, said composition comprising:
   a predetermined amount of a fibrous agent comprising psyllium husks,
   a predetermined amount of natural marine shellfish extract,
   a predetermined amount of acacia,
   a predetermined amount of fruit or vegetable pectin, and
   a predetermined amount of ascorbic acid.

2. A chemical composition as recited in claim 1 further comprising a predetermined amount of magnesium stearate.

3. A chemical composition as recited in claim 1 wherein said psyllium husks comprise an amount of generally about 80% by weight of said chemical composition; said natural marine shellfish extract generally in an amount of about 10% by weight of said chemical composition; said acacia generally in an amount of about 5% by weight of said chemical composition; said fruit or vegetable pectin generally in an amount of about 2% by weight of said chemical composition, and said ascorbic acid generally in an amount of about 2% by weight of said chemical composition.

4. A chemical composition as recited in claim 3 further comprising magnesium stearate generally in an amount of about 1% by weight of said chemical composition.

5. A chemical composition as recited in claim 1 wherein said composition is formed into a capsule containing between about 500 and 700 milligrams of said chemical composition.

6. A chemical composition as recited in claim 1 wherein said composition is formed into a capsule containing about 500 milligrams of said chemical composition.

7. A chemical composition as recited in claim 1 wherein said psyllium husks are present generally in an amount of between 72% and 88% by weight of said chemical composition; said natural marine shellfish extract is present generally in an amount of between 9% and 11% by weight of said chemical composition; said acacia is present generally in an amount of between 4.5% and 5.5% by weight of said chemical composition; and said fruit or vegetable derived pectin is present generally in an amount of between 1.4% and 2.2% by weight of said chemical composition; and said ascorbic acid is present generally in an amount of between 1.8% and 2.2% by weight of said chemical composition.

8. A chemical composition as recited in claim 7 further comprising magnesium stearate generally in an amount of about 1% by weight of said composition.

9. A chemical composition as recited in claim 7 comprising a single dose of said chemical composition being defined by about seven hundred milligrams of said composition.

10. A chemical composition as recited in claim 9 wherein said single dose comprises a capsule.

11. A method of absorbing and binding undigested fat ingested by a human and for rapidly eliminating same from the human, said method comprising:
   forming a capsule containing between about 500 and 700 milligrams of said chemical composition as recited in claim 1, and
   having the human ingest at least one of said capsules with generally about eight ounces of water generally about fifteen minutes before a meal.

12. A method of absorbing and binding undigested fat ingested by a human and for rapidly eliminating same from the human, said method comprising:
   forming a plurality of capsules each containing about 500 milligrams of a chemical composition including,
      psyllium husks generally in an amount of about 80% by weight of said chemical composition,
      natural marine shellfish extract generally in an amount of about 10% by weight of said chemical composition,
      acacia in generally an amount of about 5% by weight of said chemical composition,
      fruit or vegetable pectin generally in an amount of about 2% by weight of said chemical composition, and
      ascorbic acid generally in an amount of about 2% by weight of said chemical composition; and
   having the human ingest at least one of said plurality of capsules with generally about eight ounces of water generally about fifteen minutes before a meal.

13. A method as recited in claim 12 wherein said chemical composition further comprises magnesium stearate generally in an amount of about 1% by weight of said chemical composition.

14. A method as recited in claim 12, wherein the human ingests two of said capsules.

15. A method as recited in claim 12, wherein the human ingests three of said capsules.

16. A method as recited in claim 12, wherein the human ingests four of said capsules.

17. A method as recited in claim 12, further comprising the step of having the human ingest generally about eight ounces of water upon waking up in the morning.

18. A method as recited in claim 12, further comprising the step of having the human ingest generally about eight ounces of water between meals.

19. A chemical composition which aids in absorbing and binding undigested fat, said composition comprising:
   an amount of psyllium husks of generally about 80% by weight of said composition,
   an amount of natural marine shellfish extract of generally about 10% by weight of said composition,
   an amount of acacia of generally about 5% by weight of said composition,
   an amount of apple pectin of generally about 2% by weight of said composition, and
   an amount of ascorbic acid of generally about 2% by weight of said composition.

20. A chemical composition as recited in claim 19 further comprises an amount of magnesium stearate of generally about 1% by weight of said composition.

21. A chemical composition which aids in absorbing and binding undigested fat, said composition comprising:
   an amount of psyllium husks of generally between 72% and 88% by weight of said composition,
   an amount of natural marine shellfish extract of generally between 9% and 11% by weight of said composition,
   an amount of acacia of generally between 4.5% and 5.5% by weight of said composition,
   an amount of apple pectin of generally between 1.4% and 2.2% by weight of said composition, and
   an amount of ascorbic acid of generally between 1.8% and 2.2% by weight of said composition.

22. A chemical composition as recited in claim 21 further comprising an amount of magnesium stearate of generally about 1% by weight of said composition.

23. A method of adsorbing and binding undigested fat in a human body, said method comprising:
   forming a single dose of a chemical composition comprising,
      an amount of psyllium husks of generally between 72%. and 88% by weight of said composition,
      an amount of natural marine shellfish extract of generally between 9% and 11% by weight of said composition,
      an amount of acacia of generally between 4.5%. and 5.5% by weight of said composition,
      an amount of apple pectin of generally between 1.4% and 2.2% by weight of said composition,
      an amount of ascorbic acid of generally between 1.8% and 2.2% by weight of said composition; and
   having a human ingest at least one of said single doses prior to a meal.

24. A method as recited in claim 23 comprising forming said single dose by further including an amount of magnesium stearate of generally about 1% by weight of said composition.

25. A method as recited in claim 23 comprising having the human ingest an amount of about 2,800 milligrams of said composition prior to each meal.

26. A method as in claim 23 comprising defining said single dose to be an amount of about 700 milligrams.

27. A method as in claim 21 comprising having a human ingest at least four doses of said composition before each meal.

28. A method as in claim 23 wherein said single dose is in capsule form.

* * * * *